United States Patent
Han et al.

(10) Patent No.: US 11,633,951 B2
(45) Date of Patent: Apr. 25, 2023

(54) PRINTING DEVICE AND COMPOSITION COMPRISING MAGNETIC-COLOR-CHANGEABLE MICROCAPSULES

(71) Applicant: Société BIC, Clichy (FR)

(72) Inventors: Seung Hun Han, Gyeonggi-do (KR); Jeongmi Ha, Gyeonggi-do (KR); Jin Sung Cha, Gyeonggi-do (KR); Woo Yong Jung, Gyeonggi-do (KR); Jiyoung Ryu, Gyeonggi-do (KR); Jae Hyun Joo, Gyeonggi-do (KR)

(73) Assignee: Société BIC, Clichy (FR)

( * ) Notice: Subject to any disclaimer, the term of this patent is extended or adjusted under 35 U.S.C. 154(b) by 278 days.

(21) Appl. No.: 17/045,301

(22) PCT Filed: Apr. 5, 2019

(86) PCT No.: PCT/EP2019/058677
§ 371 (c)(1),
(2) Date: Oct. 5, 2020

(87) PCT Pub. No.: WO2019/193169
PCT Pub. Date: Oct. 10, 2019

(65) Prior Publication Data
US 2021/0146684 A1 May 20, 2021

(30) Foreign Application Priority Data
Apr. 5, 2018 (KR) .......................... 10-2018-0039860

(51) Int. Cl.
*B41J 2/10* (2006.01)
*B41J 11/00* (2006.01)
(Continued)

(52) U.S. Cl.
CPC .............. *B41J 2/10* (2013.01); *B41J 11/002* (2013.01); *B43K 8/00* (2013.01); *C09D 11/101* (2013.01); *C09D 11/50* (2013.01)

(58) Field of Classification Search
CPC . B41J 2/035; B41M 5/20; B41M 3/14; B41M 5/287; B82Y 30/00; C09D 11/50;
(Continued)

(56) References Cited

U.S. PATENT DOCUMENTS

| 4,758,275 A | * | 7/1988 | Yubakami | ............... H01F 1/445 347/53 |
| 9,606,413 B2 | * | 3/2017 | Jang | ....................... B01J 13/185 |

(Continued)

FOREIGN PATENT DOCUMENTS

| EP | 2463111 | 6/2012 |
| EP | 2848408 | 3/2015 |
| EP | 3081288 | 10/2016 |
| KR | 10-0953578 | 4/2010 |
| KR | 10-0988651 | 10/2010 |

(Continued)

OTHER PUBLICATIONS

International Search Report dated Jul. 11, 2019 in corresponding PCT Patent Application No. PCT/EP2019/058677, 6 pages.
(Continued)

*Primary Examiner* — John Zimmermann
(74) *Attorney, Agent, or Firm* — Ruggiero, McAllister & McMahon, LLC (57) ABSTRACT

This disclosure relates to a printing device for printing or dispensing a curable printing composition which is capable of changing color in response to the application of a magnetic field in the non-cured state. The printing device may be a handheld device such as a portable pen. The present disclosure further relates to curable compositions, cartridges and methods which may be used in combination with the aforementioned printing devices or in other applications.

19 Claims, 4 Drawing Sheets
(4 of 4 Drawing Sheet(s) Filed in Color)

(51) Int. Cl.
  *B43K 8/00* (2006.01)
  *C09D 11/101* (2014.01)
  *C09D 11/50* (2014.01)

(58) Field of Classification Search
  CPC ......... C09D 11/101; C09D 11/30; H01F 1/44;
  H05K 3/1275
  See application file for complete search history.

(56) References Cited

U.S. PATENT DOCUMENTS

| | | | |
|---|---|---|---|
| 2004/0170352 A1* | 9/2004 | Summers | B82Y 20/00 385/16 |
| 2011/0298880 A1 | 12/2011 | Joo et al. | |
| 2012/0236090 A1 | 9/2012 | Iftime et al. | |
| 2014/0209691 A1* | 7/2014 | Finn | H01F 27/363 235/492 |

FOREIGN PATENT DOCUMENTS

| KR | 10-2015-0020491 | 2/2015 |
|---|---|---|
| WO | 01/87629 | 11/2001 |
| WO | 2017/074152 | 5/2017 |

OTHER PUBLICATIONS

Written Opinion dated Jul. 11, 2019 in corresponding PCT Patent Application No. PCT/EP2019/058677, 8 pages.

* cited by examiner

Magnetic force

PRINTING DEVICE AND COMPOSITION COMPRISING MAGNETIC-COLOR-CHANGEABLE MICROCAPSULES

CROSS REFERENCE TO RELATED APPLICATION(S)

This application is a National Stage Application of International Application No. PCT/EP2019/058677, filed on Apr. 5, 2019, now published as WO2019/193169 and which claims priority to Korean Application No. 10-2018-0039860, filed on Apr. 5, 2018, the entire contents of which is incorporated herein by reference.

BACKGROUND OF THE DISCLOSURE

Technical Field

The present disclosure relates to a printing device, in particular a handheld printing device such as a pen, for printing a composition comprising magnetic-color-changeable microcapsules onto a printing medium. The present disclosure further relates to cartridges containing such compositions, printing methods using such compositions or cartridges, and to the compositions as such.

Description of the Related Art

Typically, a printing medium is printed with a color through a printing process including appropriate mixing of ink, toner or the like containing a pigment of a specific color and adsorption thereof onto the printing medium. In order to realize various colors through such printing, a plurality of inks or toners for basic colors is required. In the case of a printing device, red, green, blue and black cartridges are mounted and mixed to thereby realize various colors.

In order to print various colors with a single cartridge by improving such a conventional printing method, the present applicant has disclosed a printing device through Korean Patent Nos. 10-0953578 and 10-0988651, in which ink containing magnetic-color-changeable microcapsules is jetted onto a printing medium in the state in which an electric field or a magnetic field is applied to the medium, thereby exhibiting color-changing effects.

Using such a printing device, the color-changeable ink is printed using a single cartridge, and during the printing, the color is adjusted to thus exhibit a desired color. Based on the principle by which photonic crystals that constitute the magnetic-color-changeable microcapsules are arranged differently depending on the magnetic field strength to thereby vary the wavelength of reflected light, photonic crystals are arranged, after which a curable solvent surrounding the photonic crystals is cured and, thus, the mobility of the arranged photonic crystals is reduced, whereby a desired color is realized depending on the arrangement of photonic crystals upon the adsorption and curing of the ink onto the printing medium.

The applicant has attempted to develop diverse printing devices based on the above principle, but it is difficult to realize real-world applications thereof because the curable solvent, in which photonic crystals, which are nanoparticles, are dispersed, may inhibit the movement of the photonic crystals, making it difficult to achieve a desired arrangement. Moreover, the arrangement of photonic crystals and, thus, the color effect, may be disturbed by an external magnetic field even after the curing process.

The present disclosure seeks to remedy those drawbacks, at least in part.

SUMMARY OF THE DISCLOSURE

In one aspect, the present disclosure is directed towards a device for printing a composition onto a printable medium. The device may comprise a cartridge which includes a composition comprising magnetic-color-changeable microcapsules. The magnetic-color-changeable microcapsules may include a curable solvent in which electrically charged particles are dispersed. The curable solvent may be curable by application of energy. The curable resin may have a weight average molecular weight of about 100 g/mol to about 1,000 g/mol. The curable solvent may have a viscosity of about 5 to about 50 cps measured at about 25° C. The device may comprise an ejection unit for ejecting the composition from the cartridge. The device may further comprise a magnetic field generation unit for applying a magnetic field to the composition ejected from the ejection unit. The device may also comprise an energy regulation unit for generating and/or blocking energy for curing the composition ejected from the ejection unit. The energy generated from the energy regulation unit may be any one selected from among thermal energy, light energy, and chemical energy, or a combination thereof.

In a further aspect, the present disclosure is directed towards a composition for printing onto a printable medium comprising magnetic-color-changeable microcapsules. The magnetic-color-changeable microcapsules may include a curable solvent in which electrically charged particles are dispersed. The curable solvent may be cured by application of energy. The curable resin may have a weight average molecular weight of about 100 to about 1,000. The curable solvent may have a viscosity of about 5 to about 50 cps measured at about 25° C. The curable resin may be curable by energy selected from any one among thermal energy, light energy, and chemical energy, or a combination thereof.

In a further aspect, the present disclosure is directed towards a cartridge include the afore-mentioned composition. The cartridge may advantageously be usable for the aforementioned printing device.

In a further aspect, the present disclosure is directed towards a method of printing the afore-mentioned composition onto a printable medium. The method may comprise the step of ejecting the composition onto a printable medium. The method may comprise applying a magnetic field to the composition to control the color of the magnetic-color-changeable microcapsules. The method may comprise the step of curing the ejected composition. The curing may be initiated by any one of thermal energy, light energy, or chemical energy, or a combination thereof. These steps may be performed in any order and may overlap timewise.

In a further aspect, the present disclosure is directed towards a printed medium comprising the afore-mentioned composition in its cured state.

The present disclosure provides compositions, and a printing device using the same, in which, during the curing of the composition, the color-changing effects of magnetic-color-changeable microcapsules may be obviously exhibited, and in which the obtained color may be maintained stable on a printing medium even after the printing process. The color may even be stable after re-exposing the cured microcapsule to magnetic fields which are equally strong or, in some instances, even stronger than the magnetic fields used to change the color of the magnetic-color-changeable microcapsules.

These properties make the composition in particular useful for printing devices in which dispensation and curing has to be very fast and in which re-exposure of ejected composition to magnetic fields is likely. For instance, in case of a handheld writing device, in particular a portable pen, the dispensed curable composition has to cure fast in order not to accidentally stick to the user's hand and to avoid smearing. At the same time, the user may repeatedly pass over or write in the vicinity of cured composition potentially re-exposing the dispensed cured composition to magnetic fields. Under such circumstances, the presently claimed composition may be advantageous used. While the above example refers to a printing device, more specifically a handheld writing device, it should be understood that the present disclosure is not limited to these embodiments.

In some embodiments, the microcapsules may be configured to vary the spacing between the particles depending on a change in strength or direction of the magnetic field generated from the magnetic field generation unit. Additionally or alternatively, the spacing between the particles may be controllable by application of a magnetic field, and a wavelength of light reflected from the particles may vary depending on a change in the spacing.

In some embodiments, the printing device the magnetic field generation unit of the printing device may be configured to generate the magnetic field before or after adsorption of the composition to a surface of the printable medium.

In some embodiments, the particles may be electrically charged as they are or may be electrically charged by varying properties of the particles.

In some embodiments, the particles may include at least one element selected from among Fe, Co, and Ni.

In some embodiments, the resin may be either a photocurable resin and/or a thermosetting resin.

In some embodiments, the magnetic-color-changeable microcapsules may comprise a transparent capsule wall encapsulating a composition comprising electrically charged nanoparticles capable of forming a photonic crystal lattice in response to application of a magnetic field and a curable solvent comprising monomers capable of forming a cross-linked resin and a polymerization initiator.

In some embodiments the curable solvent may be composed of about 90 to about 96 wt % of the monomers capable of forming a crosslinked resin, about 1 to about 8 wt % of the polymerization initiator, and about 0.1 to about 5 wt % of a dispersant.

In some embodiments, the monomer may comprise at least two crosslinkable ene-moieties, in particular at least two acrylate or methacrylate moieties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF SPECIFIC EMBODIMENTS

Hereinafter, a detailed description will be given of the present disclosure. The terms or words used in the description and the claims of the present disclosure are not to be construed limitedly as only having common-language or dictionary meanings and should, unless specifically defined otherwise in the following description, be interpreted as having their ordinary technical meaning as established in the relevant technical field. The detailed description will refer to specific embodiments to better illustrate the present disclosure, however, it should be understood that the presented disclosure is not limited to these specific embodiments.

According to the present disclosure, a composition, especially a composition comprising magnetic-color-changeable microcapsules, suitable for use in the cartridge of a printing device, may be provided, and the printing device may include the composition and may be configured such that a magnetic field and energy for curing are applied.

Figure 1:
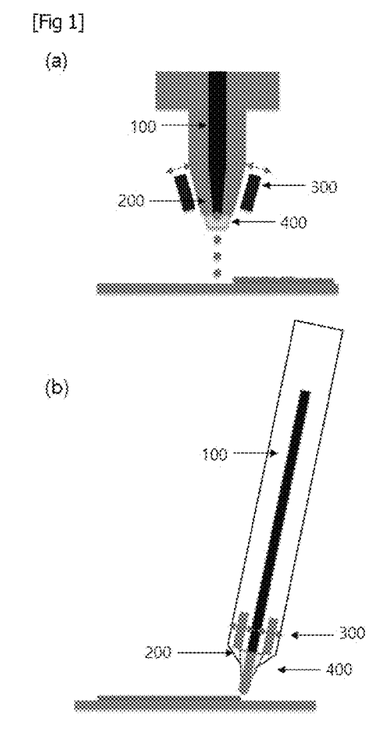
FIGS. 1A and 1B conceptually show a printing device using a composition of the present disclosure, FIG. 1A illustrating a printer head and FIG. 1B illustrating a portable pen.

As shown in FIGS. 1A and 1B, the printing device may be exemplified by an inkjet printer or a 3D printer, including a nozzle, and a cartridge-inserted portable pen. As for a printer, as exemplarily shown in FIG. 1A, when the composition is ejected from a cartridge 100 through a printer head, a magnetic field generation unit 300 is disposed around an ejection unit (nozzle) 200 and the magnetic field generation unit 300 is moved to thus control the strength of a magnetic field, whereby the spacing between particles contained in the composition may be controlled, thus realizing various colors. As for a portable pen, as exemplarily shown in FIG. 1B, a cartridge 100 including the composition is provided inside the portable pen, whereby the composition may be adsorbed onto the surface of a printing medium. Also, an energy regulation unit 400 may be provided to the tip of the pen or nozzle so that the composition may be adsorbed onto the surface of the printing medium and then cured.

The energy regulation unit 400 enables the composition to change into a fixed state (e.g. solid state, cured state, semi-cured state, etc.) by applying or blocking energy to the ejected composition, whereby electrically charged particles in the microcapsules contained in the composition are immobilized in the resin matrix to thus fix the formed color. Here, energy generated from the energy regulation unit may be selected from among thermal energy, light energy, and chemical energy. In the context of the present disclosure, the term "thermal energy" may include all types of energy which have an effect on Brownian motion and, in particular, may include heat energy, ultrasonic energy, kinetic energy and pressure. In the context of the present disclosure, the term "light energy" may include UV light (e.g. UV-A, UV-B, or UV-C), visible light or IR light, but other suitable electromagnetic wavelengths are also encompassed. In the context of the present disclosure, the term "chemical" refers to reaction energy provided by chemical reactions other than the curable solution's polymerization reaction. Depending on the kind of energy, the type of curable solvent that constitutes the composition may be selected.

The ejection unit 200 is used to eject the composition onto the surface of the printing medium. In the context of the present disclosure, the printing medium is not particularly limited but may advantageously include paper substrates, plastic-based substrates, films, sheets, and other suitable materials. In the case of a printer, the composition may be ejected in the form of droplets, and in the case of a handheld writing instrument such as portable pen, the composition may be ejected and adsorbed onto the surface of the printing medium through the tip of the nib thereof, which comes into contact with the surface of the printing medium.

The ejection of the composition, the application of a magnetic field, and the application or blockage of energy may be performed by means of a control unit (not shown). In particular, the spacing between the particles varies depending on the strength of the applied magnetic field, and thus the resulting color may change. In some embodiments, the function of the control unit of the printing medium for controlling the magnetic field generation unit 300 may be regarded as very important. The magnetic field generation unit 300 may be able to change the strength and/or direction of the magnetic field. To this end, it may be designed so as to adjust the distance and/or direction of the magnet of the magnetic field generation unit 300.

There are multiple ways of immobilizing the particles in the desired spatial arrangement (e.g. as photonic crystal composed of nanoparticles) in the resin matrix of the cured microcapsule composition during the printing process: For instance, the magnetic field generation unit 300 may generate a magnetic field before the adsorption of the composition onto the surface of the printing medium, whereby the spatial arrangement of particles is determined after which the particles/microcapsules/composition may be adsorbed onto the surface of the printing medium. Curing may take place after particles/microcapsules/composition are adsorbed onto the printing medium, but it may also be initiated earlier. Alternatively, after the adsorption of the particles/microcapsules/composition onto the surface of the printing medium, a magnetic field may be applied to the printing device, and thus the arrangement of the particles contained in the microcapsules/composition adsorbed onto the surface thereof may be adjusted, once again prior to curing or after curing has been initiated. In some embodiments, immediately before adsorption of the composition, the energy regulation unit 400 may be controlled to determine the arrangement of particles and the particles/microcapsules are cured and ejected (or ejected and cured or ejected while curing) in the afore-mentioned determined arrangement. In some embodiments, after the adsorption of the composition onto the surface of the printing medium, the arrangement of particles may be adjusted by application of the magnetic field, and simultaneously energy may be generated, whereby the arranged particles are immobilized, thus completing the printing process.

As can be seen form the above examples, the order of the steps of applying the magnetic field, ejecting the composition of magnetic-color-changeable microcapsules and regulating the energy to initiate curing of the curable solvent is not particularly limited. Likewise, the devices of the present disclosure may be configured to execute these steps in any order. In this context, it should be understood that the phrase "a magnetic field generation unit for applying a magnetic field to the composition ejected from the ejection unit" is not be construed as only allowing applying a magnetic field after ejection of the composition from the ejection unit but, rather, as also referring to the composition which may be ejected after the magnetic field was applied or during application of the magnetic field. The same applies to the term "an energy regulation unit for generating and/or blocking energy for curing the composition ejected from the ejection unit".

Unlike the conventional technique, in the present disclosure, electrically charged particles are dispersed in a microcapsule to thus form a magnetic-color-changeable microcapsule. In the context of the present disclosure, the term "magnetic-color-changeable microcapsule" is to be understood as referring to microcapsules comprising particles which are configured to change the color of the microcapsules in response to a change to the magnetic field experienced by the particles. The term "magnetic-color-changeable microcapsules" encompasses in particular microcapsules containing particles which are configured to vary the spacing between the particles depending on a change in strength and/or direction of the magnetic field generated from the magnetic field generation unit 300. Alternatively, the term "magnetic-color-changeable microcapsules" may refer to microcapsules containing electrically charged nanoparticles which are capable of self-assembling to a photonic crystal in response to application of a magnetic field and wherein the color or color intensity of the assembled particles changes in response to changes of the magnetic field.

It should be understood that the particles dispersed in the microcapsules are very small in size and, thus, may be at the boundary of dispersion or suspension and true solution. The present application refers to both "dispersion" and "solution" but, for the purposes of this disclosure, these terms should be construed as being synonymous. Likewise, the present disclosure refers to "solvent", "solved", and "curable solvent" and these terms should be construed as equally encompassing dispersions, suspensions, and dispersed and suspended particles.

Figure 2:
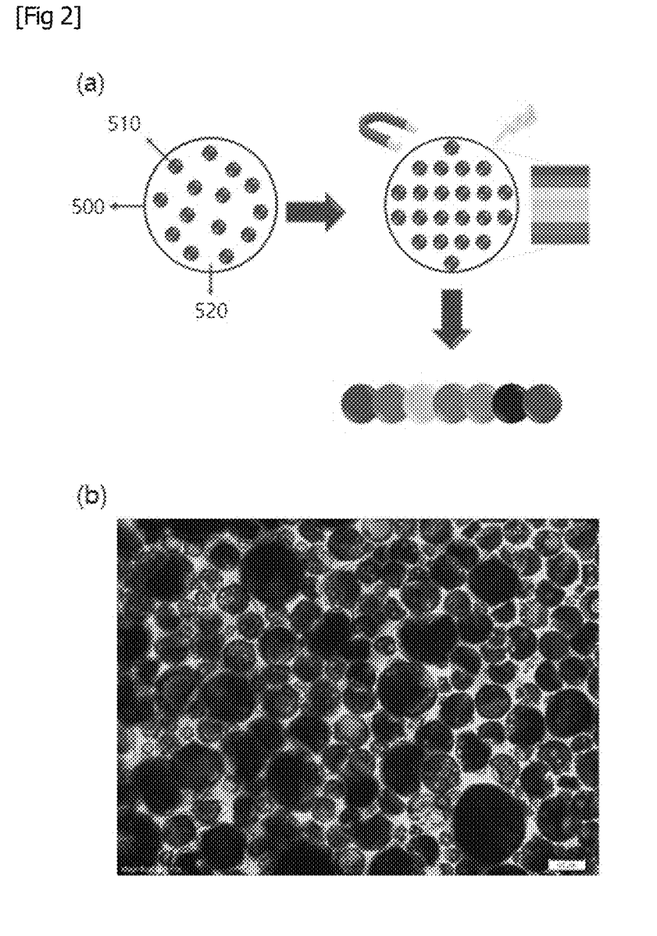
FIGS. 2A and 2B show the rearrangement in a microcapsule according to the present disclosure by means of energy and an optical microscope image of the manufactured microcapsules, respectively.

As shown in FIG. 2A, the magnetic-color-changeable microcapsule may be configured such that electrically charged particles (e.g. magnetic nanoparticles) 510 are dispersed inside a space defined by the wall of a capsule 500 formed of a transparent polymer, and the particles may be dispersed using a curable solvent 520 as a dispersion medium. Transparent in this sense should be broadly construed in view of the envisaged purpose of the microcapsule as printing medium and, in particular, encompasses transmissivity to light of wavelengths corresponding to the wavelengths reflected by the particles 510. The particles 510 dispersed in the microcapsule 500 may initially be randomly dispersed in the curable solvent 520 in a fluid state, and the spacing between the particles 510 may be adjusted by the application of an external magnetic field, thus forming a certain crystal structure. Furthermore, when energy for curing is applied thereto, the curable solvent 520 is cured, and the arranged particles may become immobilized. Thus, the particles 510 having photonic crystal characteristics reflect a wavelength in a predetermined range to thus realize a permanent and stable color.

In some embodiments, and as shown in the optical microscope image of FIG. 2B, the manufactured microcapsules may be formed to various sizes. In some embodiments, the microcapsules may have a size of about 0.5 μm to about 300 μm, in particular about 1 μm to about 100 μm, specifically about 10 to about 100 μm, or about 10 to about 50 μm, or about 10 μm to about 40 μm. The microcapsules may generally have a spherical or substantially spherical shape and, thus, their size can be determined by conventional means such as microscopy or electron microscopy. In these cases, the measured 2-dimensional representation of the microcapsule diameter may be seen as representative for the afore-mentioned size of the microcapsules.

In some embodiments, the microcapsules may have an average particle size of about 2 to about 100 μm, in particular about 3 to about 20 μm, in particular about 4 to about 10 μm. The average particle size may be determined as described in the preceding paragraph.

In some embodiments, the particle size may also be relatively uniformly distributed. This may further improve color impression by avoiding macroscopic irregularities. In some embodiments, the particle size distribution may be characterized by a D50 of about 20 μm.

In some embodiments, the particles dispersed in the capsules by the application of the external magnetic field may be provided in the form of a consistent array regardless of the size of the capsule, thus exhibiting a specific permanent and stable color.

In some embodiments, there is provided a printing device using the aforementioned cartridge comprising an aforementioned composition, comprising: a cartridge including the composition;

an ejection unit for ejecting the composition from the cartridge; a magnetic field generation unit for applying a magnetic field to the composition ejected from the ejection unit; and an energy regulation unit for generating and blocking energy for curing the composition ejected from the ejection unit.

Although the specific permanent and stable color may be shown upon the curing of the medium containing photonic crystals by the external energy in the conventional technique, the arrangement of such particles was found to be reversible, and the color may change even after the curing process by the application of an external magnetic field. This may be undesirable. According to the present disclosure, the microcapsules further contain a curable solvent which may facilitate the immobilization of the particles. It was surprisingly found that color formation during application of the magnetic field and color retention in the cured composition may be improved if the resin contained in the curable solvent has a weight-average molecular weight of about 100 g/mol to about 1,000 g/mol and the curable solvent has a viscosity of about 5 to about 50 cps measured at about 25° C. Without wishing to be bound by theory, these effects can be rationalized as follows:

The weight average molecular weight of the molecules constituting the curable solvent is associated with their size. If the weight average molecular weight thereof is too large, the density of the cured resin matrix in the microcapsule may be too low so that particles may be able to move within the resin matrix which may hinder attaining a permanent and stable color. On the other hand, if the weight average molecular weight thereof is too low, the same behavior as in a typical organic solvent may be exhibited, and thus the curing rate upon application of external energy may be remarkably decreased, making it difficult to apply to a printing device. That is, after the adsorption of the composition onto the printing medium, external energy may have to be applied for a long period of time in order for curing to take place, making it difficult to realize rapid printing.

The viscosity of the curable solvent is also regarded as important. If the viscosity thereof is too low, the motion of particles may become excessively large, and thus the arrangement of particles may be disturbed upon the application of the external magnetic field even after the curing process, making it difficult to realize a permanent and stable color. On the other hand, if the viscosity thereof is too high, the motion of particles may become excessively low, and thus the particles may not be efficiently rearranged by the application of an external magnetic field, and color sharpness may decrease.

In the following, the components and properties of the curable solvent will be discussed in more detail.

The resin contained in the curable solvent has a weight-average molecular weight of about 100 g/mol to about 1,000 g/mol. It should be understood that when reference is made to a "resin" contained in the curable solvent, the term "resin" should be broadly construed and is in particular meant to not only include polymers but also to include monomers and oligomers (number of repeat units=2 to 8). In case of polymers and oligomers, the term "weight-average molecular weight" refers to the molecular weight of each repeat unit. In case of monomers, the term refers to the molecular weight of the entire monomer.

In some embodiments. the resin contained in the curable solvent may have a weight-average molecular weight of about 100 g/mol to about 800 g/mol, in particular about 100 g/mol to 600 g/mol, specifically about 100 g/mol to 400 g/mol.

In some embodiments, the resin may be composed of mixtures of multiple components. In those cases, the weight-average molecular weight of the resin is meant to refer to the (weight-average) molecular weight of the curable components (i.e. excluding polymerization initiators and additives such as a dispersant) and each such component, by itself, has to satisfy the molecular weight requirement. To give an example: The curable solvent is composed of 94 wt.-% 1,6-hexanediol diacrylate, 3 wt.-% of poly(methyl methacrylate) having a molecular weight of about 5,000, 2 wt. % dispersant and 1 wt.-% of a photopolymerization initiator. A curable solvent comprising such a resin would have the required weight-average molecular weight of about 100 g/mol to about 1,000 g/mol since the weight-average molecular weight of poly(methyl methacrylate) resin is about 100 g/mol, the molecular weight of 1,6-hexanediol diacrylate is about 226 g/mol and the dispersant and the photopolymerization initiator are not relevant.

In some embodiments, the resin of the curable solvent may comprise monomers capable of forming a crosslinked resin. Such crosslinking may further facilitate the entrapment of the particles in the cured resin matrix and improve color stability. In some embodiments, the monomer capable of forming a crosslinked resin may be a monomer having at least two reactive functional groups. An exemplary definition of a "reactive functional group" in the aforementioned sense is a chemical group which is capable of forming a covalent bond with another (not necessarily the same) functional group under the applied polymerization conditions. Examples include crosslinkable ene-moieties, in particular acrylate and methacrylate moieties, epoxy moieties, amino moieties, thiol moieties, and isocyanate moieties.

Of course, it is also possible to use mixtures, for instance UV-activated thiol/ene-click chemistry.

In some embodiments, the curable solvent including a resin comprising a monomer which comprises at least two crosslinkable ene-moieties, in particular at least two acrylate or methacrylate moieties. In some embodiments, the monomer comprises at least two crosslinkable ene-moieties and each of the crosslinkable ene-moieties in the monomer is spaced less than 16, in particular less than 14, specifically less than 12, atoms apart, wherein the afore-mentioned atoms are selected among C, N, O, and S.

The curable solvent has a viscosity of about 5 to about 50 cps measured at about 25° C., in particular about 5 to about 40 cps, specifically about 5 to about 30 cps. In some embodiments, the curable solvent may have a viscosity, measured at about 25° C., of about 15 to about 50 cps, in particular of about 20 to about 50 cps, specifically about 25 to about 50 cps. The viscosity may be a dynamic viscosity determined using a Brookfield viscosimeter (such as a Brookfield DV2T) at about 25° C., using spindle SC4-31 at about 200 rpm and %-torque values of about 25 to about 35%.

In some embodiments, the curable solvent may be composed of a resin, a polymerization initiator, and additives, such as a dispersant. In some embodiments, the curable solvent may be composed of a resin, a polymerization initiator, and a dispersant.

In some embodiments, the resin may include a photocurable resin or a thermosetting resin. The resin may also be a photocurable thermosetting resin.

In some embodiments, the photocurable resin may include any one selected from among an acrylic resin, a methacrylic resin, an acrylic monomer, a methacrylic monomer, an acrylic monomer radical, a methacrylic monomer radical, an acrylic oligomer, and a methacrylic oligomer, each of which has a carbon double bond. Also, the thermosetting resin may include any one selected from among a phenol resin, a urea resin, a melamine resin, a silicone resin, an epoxy resin, a urethane resin, and an unsaturated polyester resin.

Also, the polymerization initiator may be a photopolymerization initiator or a thermal polymerization initiator. The photopolymerization initiator may include any one selected from among 1-hydroxycyclohexylphenylketone, bis(2,4,6-trimethylbenzoyl) phenylphosphine oxide, 2-methyl-1-[4-(methylthio)phenyl]-2-morpholinopropan-1-one, and 2,4-diethylthioxanothone. The thermal polymerization initiator may include any one azo compound selected from among 2,2'-azobis(isobutyronitrile), 1,1'-azobis(cyclohexane carbonitrile), 2,2'-azobis(2,4-dimethylvaleronitrile), 2,2'-azobis(methylbutyronitrile), di-tert-butyl peroxide, lauroyl peroxide, benzoyl peroxide, tert-butyl peroxide, azo-tert-butane, azo-bis-isopropyl, azo-normal-butane, di-tert-butyl peroxide, 2,2'-azobis(N-butyl-2-methylpropionamide), and 2,2'-azobis(N-cyclohexyl-2-methylpropionamide).

The curable solvent may contain a dispersant, thereby improving the dispersibility of individual components of the solvent. Examples of the dispersant may in particular include wet dispersants, such as BYK-154, BYK-2095, BYK-9077, and the like.

In some embodiments, the curable solvent may further include other additives, for instance rheologic modifiers, wetting agents, and adhesion promoting agents. Some examples of adhesion promoting agents include, in particular, an epoxy resin having an ether bond, a urethane adhesive having a urethane bond, or a urethane monomer.

The individual components may be used in any amount. In some embodiments, the curable solvent may be composed of 90 to 96 wt % of the resin, 1 to 8 wt % of the polymerization initiator, and 0.1 to 5 wt % of the dispersant.

Within the above ranges, it is easy to adjust the viscosity to a desired level depending on the molecular weight of the resin. It is possible to perform the preparation process even for a curable solvent falling outside of the above ranges, so long as the properties of the curable solvent are satisfied.

In some embodiments, the curable solvent may be composed of about 90 to about 96 wt % of monomers, about 1 to about 8 wt % of a polymerization initiator, and about 0.1 to about 5 wt % of one or more additives. In some embodiments, the curable solvent may comprise or consist of about 90 to about 98.9 wt % monomers, about 1 to about 5 wt % of a polymerization initiator, and about 0.1 to about 5 wt % of additives. In some embodiments, the curable solvent may comprise or consist of about 90 to about 98.9 wt % of monomers, including at least one monomer capable of forming a crosslinked resin, in particular a monomer which comprises at least two crosslinkable ene-moieties; about 1 to about 5 wt % of a polymerization initiator; and about 0.1 to about 5 wt % of one or more additives.

In some embodiments, there is provided a composition comprising magnetic-color-changeable microcapsules, wherein each of the magnetic-color-changeable microcapsules is a microcapsule including a curable solvent in which electrically charged particles are dispersed, the curable solvent includes a resin cured by application of energy, the resin has a weight average molecular weight of 100 to 1,000, and the curable solvent has a viscosity of 5 to 50 cps measured at 25° C.

In the present disclosure, the electrically charged particles of the composition may be electrically charged as they are, or may be electrically charged while the properties of the particles are varied. Examples thereof may include photonic crystal particles, and photonic crystal particles may include iron (Fe), cobalt (Co), and nickel (Ni). Also, compounds, such as elements including silicon (Si), titanium (Ti), barium (Ba), strontium (Sr), lead (Pb), aluminum (Al), copper (Cu), silver (Ag), gold (Au), tungsten (W), molybdenum (Mo), zinc (Zn), zirconium (Zr), and oxides and nitrides thereof, may be used. Also, an organic polymer including at least one monomer selected from among styrene, pyridine, pyrrole, aniline, pyrrolidone, acrylate, urethane, thiophene, carbazole, fluorene, vinyl alcohol, ethylene glycol, and ethoxy acrylate, or a polymer material such as polystyrene, polyethylene, polypropylene, polyvinyl chloride, and polyethylene terephthalate, may be used.

The photonic crystal particles may be configured such that electrically non-charged particles or clusters are coated with an electrically charged material. Examples thereof may include particles the surface of which is processed (or coated) with an organic compound having a hydrocarbon group, particles the surface of which is processed (or coated) with an organic compound having a carboxylic acid group, an ester group, and an acyl group, particles the surface of which is processed (or coated) with a complex compound having a halogen element (F, Cl, Br, I, etc.), particles the surface of which is processed (or coated) with a coordinate compound having amine, thiol, and phosphine, and electrically charged particles having a radical formed on the surface thereof. In this way, when the surface of the photonic crystal particles is coated with a material such as silica, a polymer or a monomer, high dispersibility and stability of the particles in the solvent may result.

Meanwhile, the photonic crystal particles have a diameter ranging from single-digit nm to hundreds of μm, but are not necessarily limited thereto, and may be set to a particle size that may include the photonic crystal wavelength band of the visible light range by associating the refractive index of the particles and the refractive index of the solvent based on Bragg's Law when the particles are arranged at a predetermined distance by an external electric field.

Also, the photonic crystal particles may be configured to have a unique color. To this end, a specific color may be realized by controlling the oxidation number or coating with an inorganic pigment, a dye or the like. For example, an inorganic pigment applied on the photonic crystal particles may include oxides, emulsions and lactates of Zn, Pb, Ti, Cd, Fe, As, Co, Mg, Al and the like, including a chromophore, and a dye may include a fluorescent dye, an acidic dye, a basic dye, a mordant dye, a sulfide dye, a vat dye, a disperse dye, a reactive dye and the like.

Also, the photonic crystal particles may be a material having a specific structural color so as to display a specific color thereof. For example, there is a material configured such that particles such as silicon oxide ($SiO_x$), titanium oxide ($TiO_x$) or the like are uniformly arranged at a predetermined distance on the medium having a different refractive index, thus reflecting light at a specific wavelength. The particles having a photonic crystal structure may show a structural color that varies depending on the viewing angle. Thus, when a magnetic field is applied thereto, the photonic crystal particles are moved by the arrangement of magnetic particles, thereby exhibiting a structural color that varies depending on the direction and strength of the magnetic field.

Also, in order to improve the dispersibility and stability of color display particles, the surface of the particles may be coated with silica, a polymer or a monomer.

The color display particles are more specifically dispersed in a solvent, which is auxiliary means for stably maintaining the position and arrangement of the particles.

Here, the solvent should have a specific gravity different from that of the color display particles as described above to achieve the desired effect of the present disclosure.

Also, the color display particles having magnetic properties may be applied, and may be particles containing homogeneous or heterogeneous metals or oxide particles.

In the case of metal, a magnetic precursor selected from the group consisting of a metal nitrate compound, a metal sulfate compound, a metal fluoroacetoacetate compound, a metal halide compound, a metal perchlorate compound, a metal sulfamate compound, a metal stearate compound and an organometallic compound and a ligand selected from the group consisting of an alkyltrimethylammonium halide-based cationic ligand, a neutral ligand such as an alkyl acid, trialkylphosphine, trialkylphosphine oxide, alkylamine and alkylthiol, and an anionic ligand such as sodium alkyl sulfate, sodium alkyl carboxylate, sodium alkyl phosphate, and sodium acetate are dissolved in a solvent to prepare an amorphous metal gel, which is then heated so as to be phase-converted into crystalline particles.

Here, when the heterogeneous precursor is contained in this way, the magnetic properties of the finally obtained particles may be enhanced, or a variety of magnetic materials such as superparamagnetic, paramagnetic, ferromagnetic, antiferromagnetic, ferrimagnetic and antimagnetic materials may be obtained.

Also, microparticles containing the above particles therein may be prepared through a reaction in which an emulsion is formed to give a core-shell structure.

For example, the particles are dispersed in a curable solvent to produce a core material. Here, the particles may be dispersed in an amount of 0.1 to 25 wt % in the curable solvent, but they may also be dispersed in a larger amount as necessary. The core material dispersion solution is obtained using an ultrasonic disperser or a homogenizer.

Next, a prepolymer is prepared by mixing a polymer for forming the walls of the microparticles and controlling the acidity. This process may be carried out simultaneously with the process of producing a dispersion solution of color display particles. Used as the polymer for forming the walls may be a polymer precursor, which may exhibit low elasticity and is rigid, including a copolymer such as urea-formaldehyde, melamine-formaldehyde, or methyl vinyl ether-co-maleic anhydride, or a polymer such as gelatin, polyvinyl alcohol, polyvinyl acetate, a cellulose derivative, acacia, carrageenan, carboxymethyl cellulose, hydrolyzed styrene anhydride copolymer, agar, alginate, casein, albumin and cellulose phthalate. Such a polymer is controlled in hydrophilicity and hydrophobicity, and thus may surround the color display particles to thereby form walls. Furthermore, the prepolymer may be dispersed in a dispersion medium to give a dispersion solution, as in the color display particles.

Next, forming an emulsion by mixing and stirring the dispersion solution of the color display particles and the prepolymer dispersion solution of the wall material may be carried out. In order to form such an emulsion, it is necessary to optimize the ratio of the color display particles and the prepolymer, and the two dispersion solutions may be mixed at a volume ratio of 1:5 to 1:12. Also, a stabilizer may be added to improve dispersibility. Within the emulsion, the colored nanocomposite may become a dispersion phase and the wall material may become a continuous phase.

Also, an additive may be added to increase the stability of the emulsion in the above process. Such an additive may be an organic polymer having high viscosity and superior wettability after dissolution in an aqueous phase, and a specific example thereof may include at least one selected from among gelatin, polyvinyl alcohol, sodium carboxymethyl cellulose, starch, hydroxyethyl cellulose, polyvinyl pyrrolidone, and alginate.

By adjusting the pH and temperature of the emulsion thus formed, the wall material dispersion solution in a continuous phase is deposited around the magnetic-color-changeable ink in a dispersion phase, thus forming the wall of a capsule to thereby encapsulate the core material dispersion solution. That is, the encapsulation is performed using an in-situ polymerization process. In this case, an additive may be added so that the capsule wall is formed more densely to reduce the elasticity, thereby increasing the hardness of the wall material.

The type of additive to be added may be an ionic or polar material which is soluble in an aqueous phase. For example, at least one curing catalyst selected from among ammonium chloride, resorcinol, hydroquinone, and catechol may be used.

The microparticles may be prepared by the in-situ polymerization process as described above, and may also be prepared by a coacervation process or an interfacial polymerization process.

The coacervation process utilizes the oil/water emulsion of the internal and external phases. Colloidal color display particles are coacervated (agglomerated) out of the aqueous external phase and deposited as walls around the oily droplets of the internal phase through control of temperature, pH, relative concentrations and the like, thereby creating a capsule. In the coacervation process, urea-formaldehyde, melamine-formaldehyde, gelatin or arabic rubber may be used as the wall material.

The interfacial polymerization process relies on the presence of a lipophilic monomer in the internal phase, which is present as an emulsion in the aqueous external phase. The monomer in the internal phase droplets reacts with a monomer introduced into the aqueous external phase, and polymerization occurs at the interface between the internal phase droplets and the surrounding aqueous external phase, thus forming capsule walls around the droplets. Although the resulting walls are relatively thin and are permeable, this process does not require a heating process, unlike the other preparation processes, and therefore any type of dielectric liquid may be used.

The microparticles are characterized by having a uniform spherical shape of 10 to 100 μm, more specifically 10 to 50 μm, even more specifically 10 to 40 μm, with a D50 of about 20 μm. The uniformity of the capsule shape and size is set to ensure the macroscopic uniformity of the color display particles to be rearranged by the magnetic field, thereby further improving the color change and the color sharpness. Unless the uniformity of shape and size of the microparticles is ensured, even if the color display particles dispersed in the microparticles are uniformly rearranged, macroscopic irregularity increases, and ability to realize a color and control changes therein become insufficient.

In addition, the composition containing the microparticles may be composed of the microparticles and a solvent for dispersion thereof, and the same solvent as the curable solvent may be used to cure the microparticles at the same time with the application of external energy.

In addition, since the flexibility of microparticles does not affect the color changing, the microparticles are mixed with any one of a urethane resin and a water-soluble acrylic resin or a combination thereof to give a slurry. A water-soluble polymer, a water-dispersible polymer, an oil-soluble polymer, a thermosetting polymer, a thermoplastic polymer, a UV-curable polymer, and a radiation-curable polymer may be used alone or in combination.

The composition according to the present disclosure may be applied to an ink composition for a printer or an industrial printing, and can also be applied to a cosmetic composition for color makeup.

When applied to a cosmetic composition, the composition of the disclosure may be used as a cosmetic packed in a cartridge in a composition form containing a cosmetically or dermatologically acceptable medium or base. Such a composition may be provided in the form of any formulation suitable for topical application, for example, a solution, a gel, a solid, an anhydrous product of a paste, an emulsion obtained by dispersing an oil phase in a water phase, an emulsion obtained by dispersing a water phase in an oil phase, a multi-emulsion, a suspension, a microemulsion, a microcapsule, microgranule, an ionic (liposome) and nonionic vesicular dispersant, foam or an aerosol composition containing a compressed propellant. These compositions may be prepared using typical methods in the art.

The cosmetic composition may further include a fatty substance, an organic solvent, a solubilizer, a thickener, a gelling agent, a softening agent, an antioxidant, a suspending agent, a stabilizing agent, a foaming agent, a fragrance, a surfactant, water, an ionic or nonionic emulsifier, a filler, a sequestering agent, a chelating agent, a preservative, a vitamin, a blocking agent, a wetting agent, an essential oil, a dye, a pigment, a hydrophilic or lipophilic activating agent, a lipid vesicle or an adjuvant typically useful in the cosmetic or dermatological fields. The adjuvant is introduced in an amount commonly used in the cosmetic or dermatological fields.

Also, the formulation of the cosmetic composition is not particularly limited, but may be appropriately selected depending on the end use. For example, the color cosmetics that may be directly applied to the skin may be made into any one formulation selected from the group consisting of a powder, a concealer stick, a hair dye, a hair tonic, an ointment, a gel, a cream, a patch and a spray, but is not limited thereto.

To verify the effects of the composition according to the present disclosure, compositions were prepared using $Fe_3O_4$ as electrically charged particles. These compositions were prepared using component in the amounts shown in Table 1 below.

In Table 1, the unit is parts by weight.

TABLE 1

| Component | Kind | Example 1 |
|---|---|---|
| Particles | $Fe_3O_4$ | |
| Resin | 1,6-hexanediol diacrylate | 10 |
| Polymerization initiator | 1-hydroxylcyclohexylphenylketone | 85 |
| Dispersant | BYK-9077 | 4 |

Each of the two compositions prepared as shown in Table 1 was adsorbed on a glass substrate, and the magnet was brought close thereto for 1 to 3 sec to change the color, immediately after which UV light was applied using a 3 W LED, whereby curing was completed within 1 to 5 sec. The physical properties of the cured compositions were evaluated. The results are shown in Table 2 below.

TABLE 2

| | L* | Color difference | Wavelength (nm) | Reflectivity (%) |
|---|---|---|---|---|
| Example 1 | 35.95 | 20.86 | 560 | 11.60 |
| Example 2 | 46.66 | 29.11 | 580 | 24.10 |

As is apparent from the above results, it can be confirmed that the absorption wavelength band is changed by slightly varying the amount of the dispersant in the same composition. Furthermore, when the amount of the dispersant was appropriately adjusted, the color difference and the reflectivity were improved in Example 1, thereby increasing the color development effect.

Figure 3:
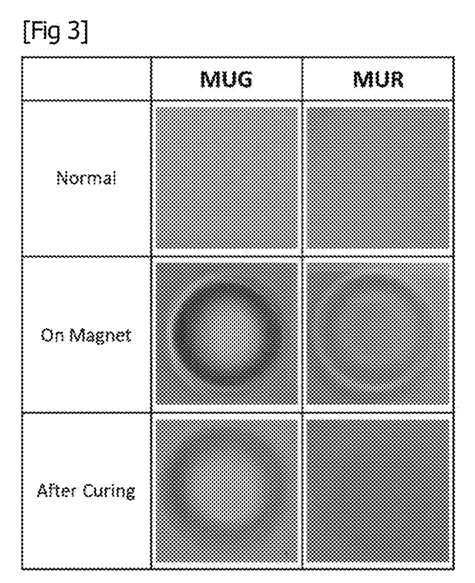
FIG. 3 shows the results of evaluation of color-changing effects of the microcapsules of the present disclosure, in which, when the color of the composition is changed to green (a) and to red (b), the normal state, the state after application of a magnetic field and the state after color fixation through curing are illustrated.

Next, in order to confirm the extent of color fixation of the composition of Example 1, the color was changed by varying the distance to which the magnet was brought close to the composition adsorbed on the glass substrate. As a result, the color was changed to green and red, as shown in FIG. 3. In any color, when the curable solvent is cured through UV irradiation after color changing by the application of a magnetic field, it can be confirmed that a unique color appears through color fixation.

Also, considering the application of the composition of the present disclosure, the color-changing effect in each step was tested, as shown in FIGS. 4A to 4D.

Figure 4:
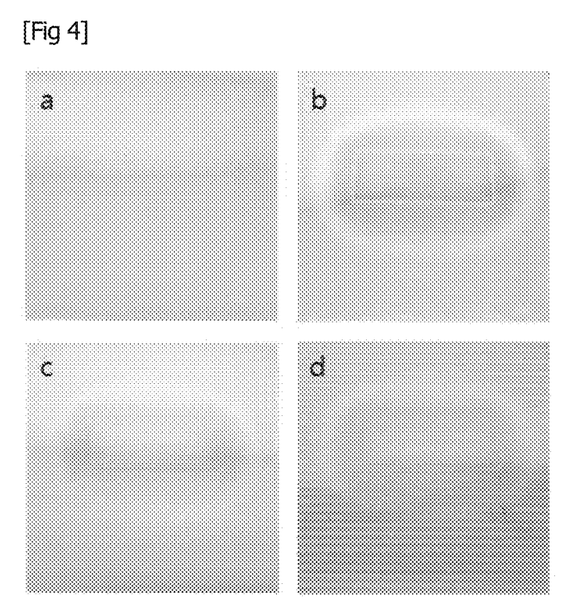
FIG. 4A shows the printing pattern before application of a magnetic field.
FIG. 4B shows the printing pattern after application of a magnetic field.
FIG. 4C shows the printing pattern upon removal of a magnetic field after UV curing.
FIG. 4D shows the printing pattern upon application of a magnetic field by bringing a rubber magnet close thereunder.

The composition was printed on a transparent film. As shown in FIG. 4A, a single color appeared before the application of a magnetic field, but as shown in FIG. 4B, the color was changed through rearrangement of the particles when a magnetic field was applied thereto by bringing a magnet close. Also, when the curable solvent was cured through UV irradiation and the magnet was then taken away, color fixation occurred, as shown in FIG. 4C. Then, when a stripe pattern was printed with the magnetic-color-changeable ink on the transparent film and a rubber magnet was then brought close thereunder, the pattern printed with the color-changeable ink appeared, as shown in FIG. 4D. However, the color change phenomenon did not occur anymore on the portion where color fixation occurred due to the curing. This result shows that the color is maintained very stable when the permanent and stable color is obtained using the composition of the present disclosure.

FIG. 4A shows the printing pattern before application of a magnetic field, FIG. 4B shows the printing pattern after application of a magnetic field, FIG. 4C shows the printing pattern when a magnetic field is removed after UV curing, and FIG. 4D shows the printing pattern when a magnetic field is applied by bringing a rubber magnet close thereunder.

Figure 5:
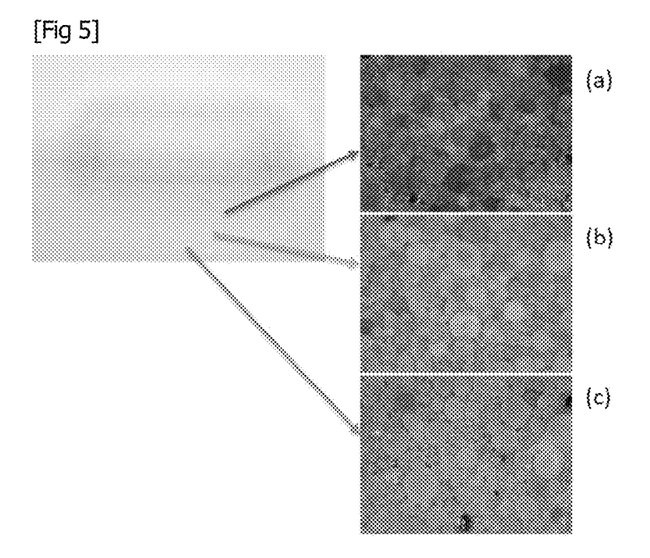
FIG. 5 shows optical microscope images of individual portions of a UV-cured printing pattern.

FIG. 5 shows optical microscope images of individual portions of the UV-cured printed pattern. As seen in the optical microscope images of portions (a) to (c) of FIG. 5, green (a), yellowish green (b) and light orange (c) are observed.

Any type of printing device may be configured using the characteristics of the composition of the present disclosure.

Figure 6:
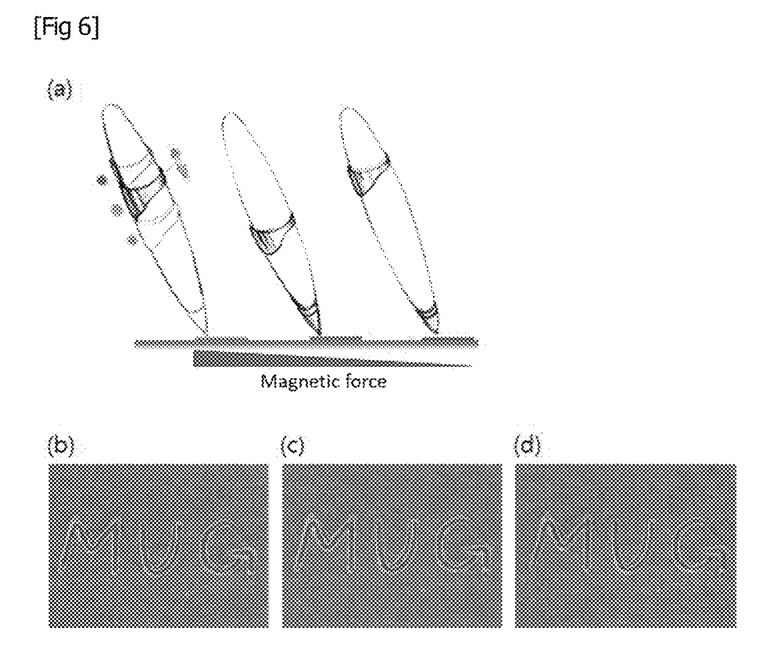
FIG. 6A shows the operation of a portable pen provided with a cartridge including the composition of the present disclosure.
FIG. 6B shows the state before application of a magnetic field upon a hand writing test with the portable pen.
FIGS. 6C and 6D show the states after application of a magnetic field and UV light, respectively.

In an embodiment, there is provided a portable pen with a cartridge containing the composition of the present disclosure. This portable pen may adjust the distance of the magnetic field generation unit by moving the switch mounted on the body of the pen up and down, thereby changing the color of the composition (FIG. 6A). Thus, a full range of structural colors may be realized through a single cartridge.

Furthermore, when the writing test is performed on paper with the portable pen, the color-changing effect can be confirmed before the application of a magnetic field (FIG. 6B), after the application of a magnetic field (FIG. 6C), and after UV irradiation (FIG. 6D), from which various colors can be found to be realized.

Therefore, the present disclosure can provide a composition that is suitable for use in various printing devices by drastically improving the stability of color changing, color fixing and permanent and stable color by solving the problems with printing methods or devices using photonic crystal characteristics according to conventional techniques, and can also provide a printing device.

Although the more specific embodiments of the present disclosure have been disclosed for illustrative purposes, those skilled in the art will appreciate that various modifications and alterations are possible, without departing from the spirit of the present disclosure. It is also to be understood that such modifications and alterations are incorporated in the scope of the present disclosure and the accompanying claims.

EXPLANATION OF SYMBOLS

100: Cartridge
200: The discharge portion
300: Magnetic field generating portion
400: Energy control unit
500: Microcapsule
510: Particle
520: Curable solvent

What is claimed is:

1. A device for printing a composition onto a printable medium comprising:
a cartridge including the composition comprising:
magnetic-color-changeable microcapsules, wherein the magnetic-color-changeable microcapsules are microcapsules including a curable solvent in which electrically charged particles are dispersed, wherein spacing between the particles is controllable by application of a magnetic field, and wherein the particles reflect a wavelength of light that varies depending on a change in the spacing, wherein the curable solvent includes a resin curable by application of energy, the resin having a weight average molecular weight of about 100 to about 800, and wherein the curable solvent has a viscosity of about 5 to about 50 cps measured at 25° C.;
an ejection unit for ejecting the composition from the cartridge;
a magnetic field generation unit for applying a magnetic field to the composition ejected from the ejection unit; and
an energy regulation unit for generating and/or blocking energy for curing the composition ejected from the ejection unit, wherein the energy generated from the energy regulation unit is any one selected from among thermal energy, light energy, and chemical energy, and wherein the printing device is a handheld writing device.

2. The printing device of claim 1, wherein the handheld writing device is a portable pen.

3. The printing device of claim 1, wherein the microcapsules are configured to vary the spacing between the particles depending on a change in strength or direction of the magnetic field generated from the magnetic field generation unit.

4. The printing device of claim 1, wherein the magnetic field generation unit is configured to generate the magnetic field before or after adsorption of the composition to a surface of the printable medium.

5. The printing device of claim 1, wherein between the particles there is a spacing that is controllable by application of a magnetic field, and wherein the particles have a wavelength of light reflected therefrom that varies depending on a change in the spacing.

6. The printing device of claim 1, wherein the particles are electrically charged as they are or are electrically charged by varying properties of the particles.

7. The printing device of claim 1, wherein the particles include at least one element selected from among Fe, Co, and Ni.

8. The printing device of claim 1, wherein the resin is a photocurable resin and/or a thermosetting resin.

9. The printing device of claim 1, wherein the magnetic-color-changeable microcapsules comprise a transparent capsule wall encapsulating a composition comprising electrically charged nanoparticles capable of forming a photonic crystal lattice in response to application of a magnetic field and a curable solvent comprising one or more monomer types capable of forming a crosslinked resin and a polymerization initiator.

10. The printing device of claim 1, wherein the curable solvent is composed of 90 to 96 wt % of one or more monomers capable of forming a crosslinked resin, 1 to 8 wt % of a polymerization initiator, and 0.1 to 5 wt % of a dispersant.

11. The printing device of claim 10, wherein the monomer comprises at least two crosslinkable ene-moieties.

12. A composition for printing onto a printable medium comprising magnetic-color-changeable microcapsules, wherein the magnetic-color-changeable microcapsules is a microcapsule including a curable solvent in which electrically charged particles are dispersed, wherein the particles have a spacing therebetween controllable by application of a magnet field, and wherein the particles reflect a wavelength of light that varies depending on a change in the spacing, the curable solvent includes a resin curable by application of energy, the energy being any one selected from among thermal energy, light energy, and chemical energy, the resin has a weight average molecular weight of about 100 to about 800, and the curable solvent has a viscosity of about 5 to about 50 cps measured at 25° C.

13. The composition of claim 12, wherein the particles are electrically charged as they are or are electrically charged by varying properties of the particles.

14. The composition of claim 12, wherein the particles include at least one element selected from among Fe, Co, and Ni.

15. The composition of claim 12, wherein the resin is a photocurable resin and/or a thermosetting resin.

16. The composition of claim 12, wherein the magnetic-color-changeable microcapsules comprise a transparent capsule wall encapsulating a composition comprising electrically charged nanoparticles capable of forming a photonic crystal lattice in response to application of a magnetic field and a curable solvent comprising one or more monomer types capable of forming a crosslinked resin and a polymerization initiator.

17. The composition of claim 12, wherein the curable solvent is composed of 90 to 96 wt % of one or more monomers capable of forming a crosslinked resin, 1 to 8 wt % of a polymerization initiator, and 0.1 to 5 wt % of a dispersant.

18. The composition of claim 12, wherein the monomer comprises at least two crosslinkable ene-moieties, in particular at least two acrylate or methacrylate moieties.

19. A method of printing the composition of claim 12 onto a printable medium, comprising in any order:
    ejecting the composition onto a printable medium,
    applying a magnetic field to the composition to control the color of the magnetic-color-changeable microcapsules,
    curing the ejected composition, wherein curing is initiated by any one selected from among thermal energy, light energy, and chemical energy.

* * * * *